(12) United States Patent
Fronticelli

(10) Patent No.: US 6,780,892 B1
(45) Date of Patent: Aug. 24, 2004

(54) POLYMERIC HEMOGLOBIN MUTANTS

(75) Inventor: Clara Fronticelli, Timonium, MD (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/787,216

(22) PCT Filed: Sep. 30, 1999

(86) PCT No.: PCT/US99/22756

§ 371 (c)(1),
(2), (4) Date: Jul. 13, 2001

(87) PCT Pub. No.: WO00/18802

PCT Pub. Date: Apr. 6, 2000

Related U.S. Application Data

(60) Provisional application No. 60/102,640, filed on Oct. 1, 1998.

(51) Int. Cl.[7] ............................................. C07K 14/00
(52) U.S. Cl. .......................................... 516/6; 530/385
(58) Field of Search ............................... 514/6; 530/385

(56) References Cited

U.S. PATENT DOCUMENTS

| | | | |
|---|---|---|---|
| 5,028,588 A | 7/1991 | Hoffman et al. | 514/6 |
| 5,239,061 A | 8/1993 | Fronticelli et al. | 530/385 |
| 5,545,727 A | 8/1996 | Hoffman et al. | 536/234 |
| 5,661,124 A | 8/1997 | Hoffman et al. | 514/6 |
| 5,753,465 A | 5/1998 | Ho et al. | 435/69.6 |

OTHER PUBLICATIONS

Chatterjee et al., *J. Biol. Chem.* 261:9929–9937, 1986.
Bucci et al., *Biochemistry* 5:3418–3425, 1996.
Jones et al., *J. Biol. Chem.* 271:675–680, 1996.
Gould et al., *Critical Care Clinics* 8:293–312, 1992.
Gould et al., *World J. Surg.* 20:1200–7, 1996.
Doyle et al., *J. Biol. Chem.* 274:2583–2591, 1999.
Looker et al., *Nature* 356:258–260, 1992.
Fronticelli et al., *J. Biol. Chem.* 270:30588–30592, 1995.
Bonaventura & Riggs, *Science*, 158:800–2, 1967.
Fronticelli et al., *J. Prot. Chem.* 10:495–501, 1991.
Sanna et al., *J. Biol. Chem.* 272:3478–3486, 1996.
Vasquez et al., *Biophysical Journal* 76:88–97, 1999.

*Primary Examiner*—Karen Cochrane Carlson
(74) *Attorney, Agent, or Firm*—Drinker Biddle & Reath LLP

(57) ABSTRACT

Human β-globin mutant polypeptides comprise the amino acid sequence of normal human β-globin modified by (i) the substitution or deletion of Cys at amino acid positions 93 and 112, and (ii) the substitution of a Cys fore a non-Cys amino acid at one other position in the polypeptide, preferable Ser at amino acid position 9. Modified human hemoglobins containing this or other β-globin mutations, and/or an α-globin mutation, are provided, as well as polymers of such modified hemoglobins. Nucleic acids, vectors, and transformed host cells for producing the β-globin mutants are provided.

21 Claims, 3 Drawing Sheets

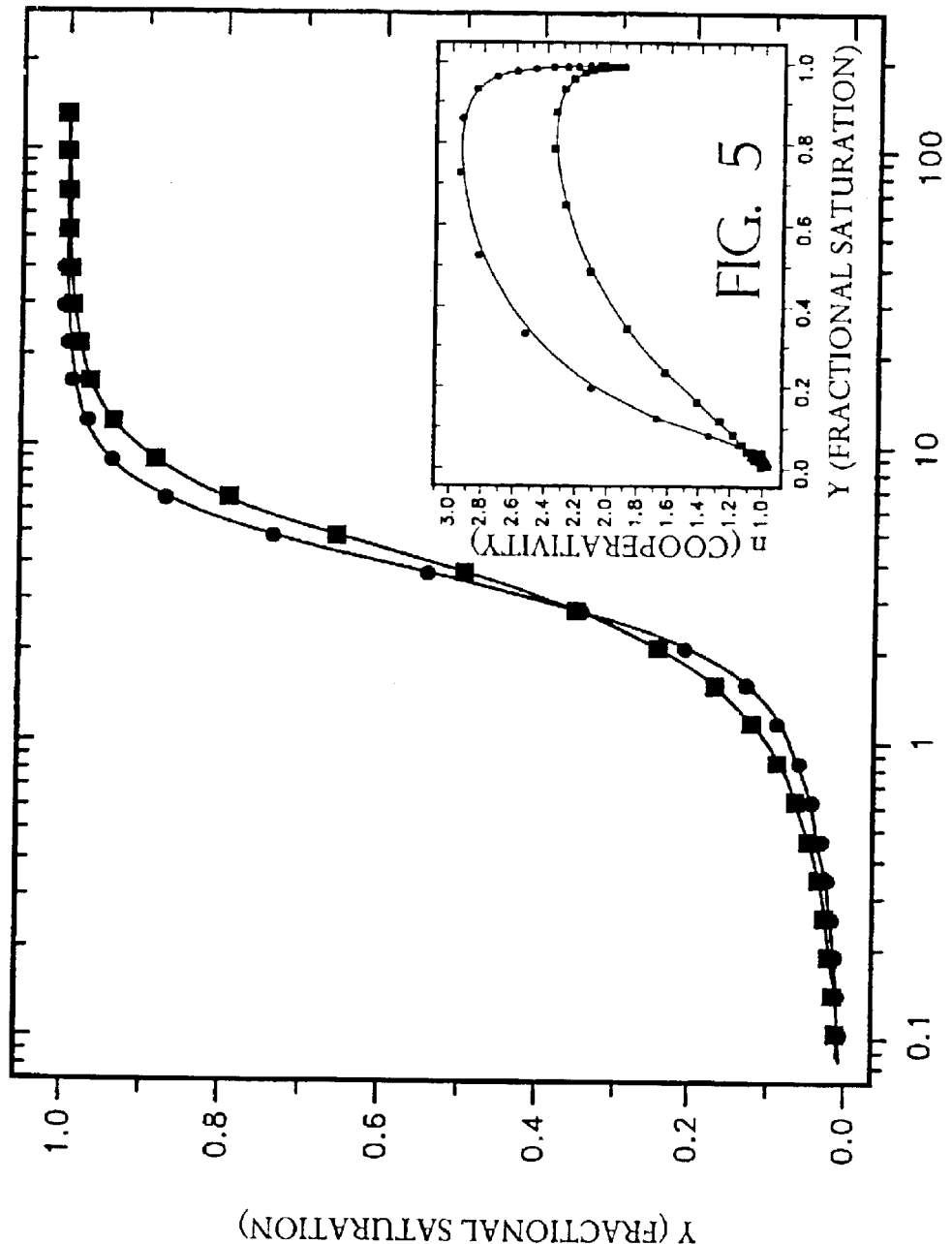

SEQUENCE LISTING

<160> NUMBER OF SEQ ID NOS: 12

<210> SEQ ID NO 1
<211> LENGTH: 438
<212> TYPE: DNA
<213> ORGANISM: Human

<400> SEQUENCE: 1

```
gtgcacctga ctcctgagga gaagtctgcc gttactgccc tgtggggcaa ggtgaacgtg      60
gatgaagttg gtggtgaggc cctgggcagg ctgctggtgg tctacccttg gacccagagg     120
ttctttgagt cctttgggga tctgtccact cctgatgctg ttatgggcaa ccctaaggtg     180
aaggctcatg gcaagaaagt gctcggtgcc tttagtgatg gcctggctca cctggacaac     240
ctcaagggca cctttgccac actgagtgag ctgcactgtg acaagctgca cgtggatcct     300
gagaacttca ggctcctggg caacgtgctg gtctgtgtgc tggcccatca ctttggcaaa     360
gaattcaccc caccagtgca ggctgcctat cagaaagtgg tggctggtgt ggctaatgcc     420
ctggcccaca agtatcac                                                   438
```

<210> SEQ ID NO 2
<211> LENGTH: 438
<212> TYPE: DNA
<213> ORGANISM: Artificial Sequence
<220> FEATURE:
<223> OTHER INFORMATION: Description of Artificial Sequence: Mutant of human beta-globin

<400> SEQUENCE: 2

```
gtgcacctga ctcctgagga gaagtgcgcc gttactgccc tgtggggcaa ggtgaacgtg      60
gatgaagttg gtggtgaggc cctgggcagg ctgctggtgg tctacccttg gacccagagg     120
ttctttgagt cctttgggga tctgtccact cctgatgctg ttatgggcaa ccctaaggtg     180
```

```
aaggctcatg gcaagaaagt gctcggtgcc tttagtgatg gcctggctca cctggacaac    240
ctcaagggca cctttgccac actgagtgag ctgcatgctg acaagctgca cgtggatcct    300
gagaacttca ggctcctggg caacgtgctg gtcggtgtgc tggcccatca ctttggcaaa    360
gaattcaccc caccagtgca ggctgcctat cagaaagtgg tggctggtgt ggctaatgcc    420
ctggcccaca agtatcac                                                  438
```

<210> SEQ ID NO 3
<211> LENGTH: 146
<212> TYPE: PRT
<213> ORGANISM: Human

<400> SEQUENCE: 3

```
Val His Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145
```

<210> SEQ ID NO 4
<211> LENGTH: 146
<212> TYPE: PRT
<213> ORGANISM: Artificial Sequence
<220> FEATURE:
<223> OTHER INFORMATION: Description of Artificial Sequence: Mutant of
      human beta-globin

<400> SEQUENCE: 4

```
Val His Leu Thr Pro Glu Glu Lys Cys Ala Val Thr Ala Leu Trp Gly
 1               5                  10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Ala Asp Lys Leu
                85                  90                  95

His Val Asp Pro Glu Asn Phe Arg Leu Leu Gly Asn Val Leu Val Gly
```

```
            100                 105                 110
Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 5
<211> LENGTH: 141
<212> TYPE: PRT
<213> ORGANISM: Human

<400> SEQUENCE: 5

Val Leu Ser Pro Ala Asp Lys Thr Asn Val Lys Ala Ala Trp Gly Lys
  1               5                  10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
 65                 70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 6
<211> LENGTH: 141
<212> TYPE: PRT
<213> ORGANISM: Artificial Sequence
<220> FEATURE:
<223> OTHER INFORMATION: Description of Artificial Sequence: Mutant of
      human alpha-globin

<400> SEQUENCE: 6

Val Leu Ser Pro Ala Asp Lys Thr Asn Val Lys Ala Ala Trp Gly Lys
  1               5                  10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
 65                 70                  75                  80

Ser Ala Leu Ser Asp Leu His Ala His Lys Leu Arg Val Asp Pro Val
                85                  90                  95

Asn Phe Lys Leu Leu Ser His Ser Leu Leu Val Thr Leu Ala Ala His
            100                 105                 110

Leu Pro Ala Glu Phe Thr Pro Ala Val His Ala Ser Leu Asp Lys Phe
```

```
            115                 120                 125
Leu Ala Ser Val Ser Thr Val Leu Thr Ser Lys Tyr Arg
    130                 135                 140

<210> SEQ ID NO 7
<211> LENGTH: 423
<212> TYPE: DNA
<213> ORGANISM: Artificial Sequence
<220> FEATURE:
<223> OTHER INFORMATION: Description of Artificial Sequence: Mutant of
      human alpha-globin

<400> SEQUENCE: 7
gtgctgtctc ctgccgacaa gaccaacgtc aaggccgcct ggggcaaggt tggcgcgcac      60
gctggcgagt atggtgcgga ggccctggag aggatgttcc tgtccttccc caccaccaag     120
acctacttcc cgcacttcga cctgagccac ggctctgccc aggttaaggg ccacggcaag     180
aaggtggccg acgcgctgac caacgccgtg gcgcacgtgg acgacatgcc caacgcgctg     240
tccgccctga gcgacctgca cgcgcacaag cttcgggtgg acccggtcaa cttcaagctc     300
ctaagccact ccctgctggt gaccctggcc gcccacctcc ccgccgagtt caccccctgcg    360 gtgcacgcct ccctggacaa gttcctggct tctgtgagca ccgtgctgac ctccaaatac     420
cgt                                                                   423

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Factor Xa
      recognition sequence

<400> SEQUENCE: 8

Ile Glu Gly Arg
  1

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:
      Mutagenizing oligonucleotide for human beta-globin Ser9-Cys
      mutation

<400> SEQUENCE: 9
ggcagtaacg gcgcacttct cctcagg                                          27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Mutagenizing oligonucleotide for human beta-globin Cys93-Ala
      mutation

<400> SEQUENCE: 10
tgcagcttgt cagcatgcag ctcactc                                          27

<210> SEQ ID NO 11
<211> LENGTH: 18
<212> TYPE: DNA
<213> ORGANISM: Artificial Sequence
```

-continued

```
<220> FEATURE:
<223> OTHER INFORMATION: Description of Artificial Sequence:
      Mutagenizing oligonucleotide for human beta-globin Cys112-Gly
      mutation

<400> SEQUENCE: 11
cagcacaccg accagcac                                                    18

<210> SEQ ID NO 12
<211> LENGTH: 423
<212> TYPE: DNA
<213> ORGANISM: Human

<400> SEQUENCE: 12
gtgctgtctc ctgccgacaa gaccaacgtc aaggccgcct ggggcaaggt tggcgcgcac       60
gctggcgagt atggtgcgga ggccctggag aggatgttcc tgtccttccc caccaccaag     120
acctacttcc cgcacttcga cctgagccac ggctctgccc aggttaaggg ccacggcaag     180
aaggtggccg acgcgctgac caacgccgtg gcgcacgtgg acgacatgcc caacgcgctg     240
tccgccctga gcgacctgca cgcgcacaag cttcgggtgg acccggtcaa cttcaagctc     300
ctaagccact gcctgctggt gaccctggcc gcccacctcc ccgccgagtt cacccctgcg     360
gtgcacgcct ccctggacaa gttcctggct tctgtgagca ccgtgctgac ctccaaatac     420
cgt                                                                   423
```

POLYMERIC HEMOGLOBIN MUTANTS

This is a 371 of PCT/US99/22756, international filing date Sep. 30, 1999, which claims the benefit of U.S. provisional patent application Ser. No. 60/102,640, filed Oct. 1, 1998. The entire disclosure of the aforesaid provisional application is incorporated herein by reference.

REFERENCE TO GOVERNMENT GRANT

The invention was supported in part by National Institutes of Health Grant HLBI P01-HL48517. The U.S. government has certain rights in the invention.

FIELD OF THE INVENTION

The invention relates to mutants of tetrameric hemoglobin molecules engineered to possess optimal oxygen carrying characteristics. The molecules are useful as blood substitutes.

BACKGROUND OF THE INVENTION

Hemoglobin is a tetrameric molecule having a molecular weight of 64,500 Daltons. It is the protein in red blood cells which transports oxygen from the lungs to the tissues. The tetrameric molecule is formed of two pairs of α and β subunits. The subunits are held together as a result of ionic, hydrophobic and Van der Waals forces, and not as a result of covalent bonds. When hemoglobin is oxygenated, i.e., combined with oxygen, it readily forms α-β dimers having a molecular weight of 32,250 Daltons. These dimers are not retained in vivo by the kidneys and are eliminated through the urine. Urine elimination is the result of the dissociation of tetrameric hemoglobins into dimers.

Hemoglobin-based oxygen carriers have been proposed as substitutes for red blood cells, as artificial oxygen-delivery agents for replacing blood transfusions. Acellular products are preferred over cell-based red blood cell substitutes since cell-free products do not require tissue typing, are easier to store than cellular products, have a longer shelf life than cellular products, and can be made virus-free. However, there are problems associated with the use of hemoglobin solutions. Hemoglobin solutions have a short retention time in circulation due to the dissociation of hemoglobin into dimers which rapidly filter through the kidney glomeruli and vasoconstriction due to depletion of nitric oxide in the wall of the vasculature, probably resulting from hemoglobin extravasation.

In human red cells, the interaction of 2,3-diphosphoglycerate (2,3-DPG) with hemoglobin regulates the efficient release of oxygen to the tissues. Inside red blood cells, 2,3-DPG combines with hemoglobin in order to decrease its oxygen affinity to a level compatible with oxygen transport. Solutions of hemoglobin thus have a high oxygen affinity due to the absence of the 2-3-DPG regulation present within red cells.

An acellular product must have a high retention time in the circulation in order to serve as a blood substitute. In order to increase the retention time, it is necessary to impede the dissociation of the tetrameric hemoglobin molecule into dimers. Several types of chemical modifications have been implemented which stabilize the tetrameric form of hemoglobin by introducing an intramolecular cross-link between either the α or the β-subunits (Chatterjee et al., *J. Biol. Chem.* 261:9929–9937, 1986; Bucci et al., *Biochemistry* 5:3418–3425, 1996; Jones et al., *J. Biol. Chem.* 271:675–680, 1996) High molecular weight polymers have also been obtained by intermolecular chemical crosslinking although these comprise a large distribution of molecules of different molecular weight (Gould et al., *Critical Care Clinics* 8:293–312, 1992; Gould et al., *World J. Surg.* 20:1200–7, 1996). However, such chemically cross-linked polymers must then be subjected to a series of complex purification steps to remove adjuvants or surfactants associated with the cross-linking process.

In order to maintain the hydric balance, solutions of tetrameric hemoglobin can not be used at a concentration higher than 7%, about half the concentration of hemoglobin in blood. Polymerization of several hemoglobin molecules makes possible the use of higher hemoglobin concentration without exceeding the normal oncotic pressure. By "polymerization" as used herein with respect to hemoglobin is meant the formation of associations of two or more hemoglobin tetramers. Polymerization also hinders extravasation of tetrameric hemoglobin molecules into the interstitial space apparently decreasing the vasoactivity of these solutions (Doyle et al., *J. Biol. Chem.* 274:2583–2591, 1999).

Polymerization of tetrameric hemoglobin as a means of impeding dissociation involves the creation of higher molecular weight polymers. However, chemically-induced polymerization results in a large distribution of molecules of different molecular weight. Such heterogenous polymers tend to have varying characteristics across a population, the properties being difficult to control. A homogenous polymer is preferable.

The development of genetic engineering has made available the expression of hemoglobins in microorganisms. Certain mutant forms of hemoglobin have been discussed in the prior art. Hoffman et al. (U.S. Pat. Nos. 5,661,124 and 5,028,588) describe beneficial mutants having a $P_{50}$ analogous to that of normal hemoglobin. The mutants are characterized by an osmolarity of greater than 303 mmol/L. Bonaventura & Riggs, *Science*, 158:800–2 (1967) describe the naturally occurring β-chain mutation "HbPorto Allegre" in which serine at position 9 is replaced with cysteine.

A recombinant mutant hemoglobin currently under clinical trials has a low oxygen affinity and the tetrameric structure stabilized by using an expression vector containing a single duplicated tandemly fused α-globin gene (Looker et al., *Nature* 356:258–260, 1992). Another mutant recombinant hemoglobin contains five amino acid substitutions and has an intrinsic low oxygen affinity that is modulated by chloride ions (Fronticelli et al., *J. Biol. Chem.* 270:30588–30592, 1995). The oxygen affinity values for this mutant are similar to those of whole blood in the presence of physiological chloride ions concentrations (120 mM).

SUMMARY OF THE INVENTION

It is an object of the invention to provide a mutant hemoglobin by recombinant DNA techniques having a high oxygen carrying capacity but low oncotic pressure useful as a blood substitute.

It is an object of the invention to provide a mutant hemoglobin which forms polymers of such hemoglobins through disulfide bonds in a controlled fashion, without interference from spurious bonds during refolding and polymerization.

It is a further object of the invention to provide a preparation of stable homogeneous polymers.

It is an object of the invention to provide for the formation of stable hemoglobin polymers without the use of exogenous synthetic chemical crosslinkers.

These and other objects of the invention will be apparent from the following disclosure.

According to the present invention, a modified human β-globin polypeptide is provided having the amino acid sequence of the normal human β-globin modified by (i) the substitution or deletion of Cys at positions 93 and 112, and (ii) the substitution of a Cys for a non-Cys amino acid at one other position. In preferred embodiments, Cys is subsisted for one of the amino acids at the following positions: (a) Ser at position 9; (b) Asn at position 80; or (c) Lys at position 17. Most preferably, Cys is subsisted for Ser at position 9. According to a preferred embodiment, the cysteine residue at position 93 is substituted with an alanine residue, and/or the cysteine residue at position 112 is substituted with a glycine residue. Where all three substitutions are present (Ser9→Cys, Cys93→Ala and Cys112→Gly), the polypeptide has the sequence SEQ ID NO:4. A hemoglobin comprising the aforesaid three-position mutant β-globin and normal α-globin is hereinafter identified as "Hb Prisca". Normal hemoglobin is referred to as "HbA". Normal hemoglobin is characterized by α- and β-globin polypeptides having the native, i.e., non-mutant or wild type, amino acid sequences.

In another aspect, the invention is directed to nucleic acid encoding the aforesaid mutant β-globin polypeptide. In preferred embodiments, the nucleic acid encodes the polypeptide of SEQ ID NO:4. In one such embodiment, the nucleic acid has the nucleotide sequence SEQ ID NO:2.

In another aspect, the invention is directed to vectors comprising a promoter operably linked to a nucleic acid sequence encoding the mutant β-globin polypeptide, capable of directing the expression of a mutant human β-globin polypeptide. The invention is further directed to host cells transformed with such vectors.

A method for producing a human β-globin mutant polypeptide is provided comprising a culture of the aforesaid transformed host cells under conditions conducive to the expression of said polypeptide by said host cells.

The invention is also directed to a modified human hemoglobin in which at least one of the β-globins, preferably both β-globins, is a modified β-globin as described above. By "hemoglobin" is meant the functional tetrameric molecule comprising two α-globin polypeptides, two β-globin polypeptides and heme. In one embodiment, the modified human hemoglobin is further characterized by the presence of an α-globin mutant polypeptide having the amino acid sequence of normal human α-globin modified by the substitution or deletion of Cys at position 104. A preferred mutation is Cys104→Ser (SEQ ID NO:6). The α-globin may be further modified by either the substitution of Cys for Ala at position 71, or the substitution of Cys for Ala at position 53. Both α-globin polypeptides of the tetrameric hemoglobin are preferably mutant.

According to one embodiment, the modified hemoglobin has all of the native Cys residues substituted by non-Cys residues, and one non-native Cys is introduced into either the α-globin or β-globin polypeptide, by substitution. Thus, a modified human hemoglobin comprises a mutant human α-globin polypeptide comprising the amino acid sequence of normal human α-globin modified by the substitution of Cys at position 104 by a non-Cys amino acid; and a mutant human β-globin polypeptide comprising the amino acid sequence of normal human β-globin modified by the substitution of Cys at positions 93 and 112 by non-Cys amino acids. The modified hemoglobin is further characterized by the substitution of Cys for the native sequence amino acid at one of the following positions: β-globin position 9; β-globin position 17; β-globin position 80; α-globin position 71; or α-globin position 53. Thus, since each hemoglobin contains two α and two β chains, each molecule of modified human hemoglobin contains two non-native Cys residues.

The invention is further directed to a polymeric hemoglobin comprising the aforesaid modified human hemoglobins. The polymer may contain, for example, from 2 to 200 hemoglobin molecules, more preferably from 2 to 40, most preferably from 2–20. In one embodiment, the modified tetrameric hemoglobins of the polymeric hemoglobin are covalently bonded to each other by one or more intermolecular disulfide bridges formed by cysteine amino acid residues. In one embodiment, the modified hemoglobin of the polymer HB Prisca, and the polymer comprises from two to seven of the modified hemoglobins The invention is also directed to an artificial blood substitute comprising the aforesaid polymeric hemoglobin, preferably in combination with a pharmaceutically acceptable carrier. A method of supplementing the oxygen-carrying capacity of a patient's blood comprises administering to the patient an effective amount of the aforesaid blood substitute.

BRIEF DESCRIPTION OF THE FIGURES

FIG. 4 shows oxygen binding curves of HbA (•) and of the heptad of Hb Prisca (■) at 110 days polymerization. The inset in FIG. 4, FIG. 5, shows the cooperativity of these hemoglobins at the different levels of oxygen saturation.

DETAILED DESCRIPTION OF THE INVENTION

Figure 1:
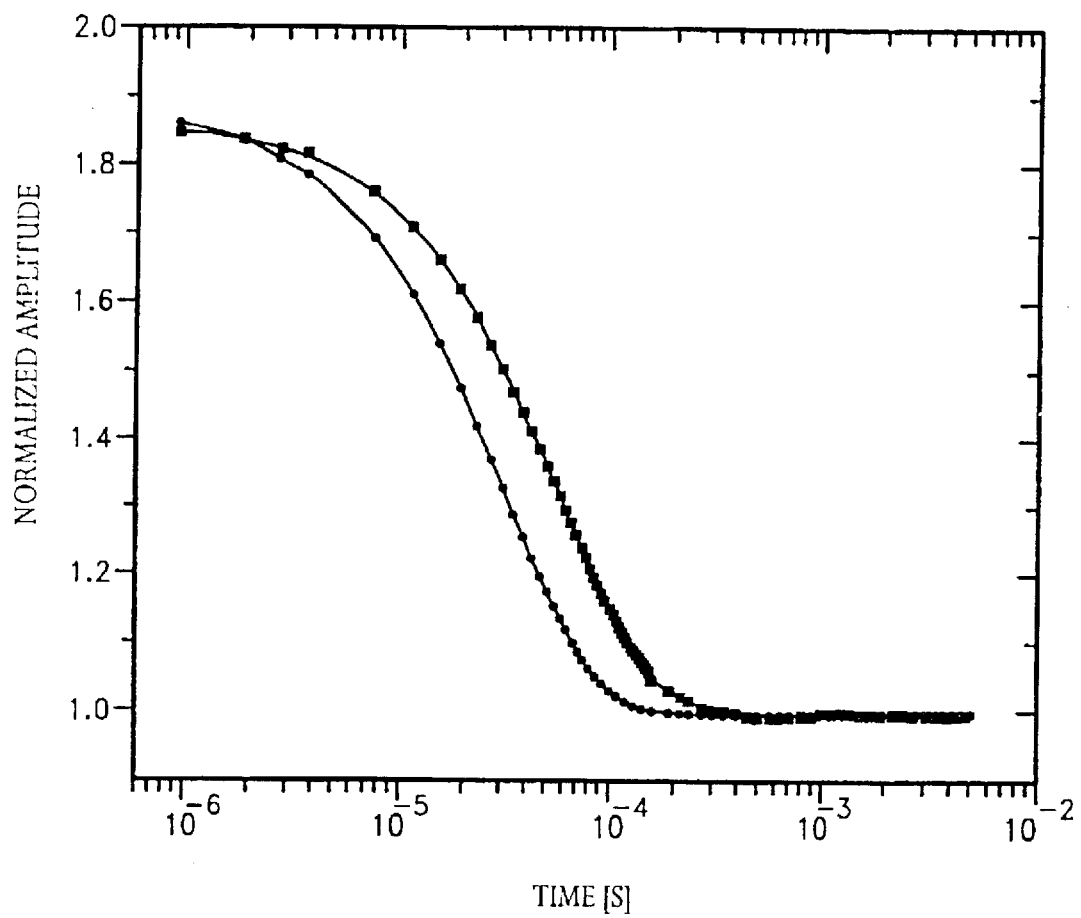
FIG. 1 shows the normalized autocorrelation function (ACF) for normal hemoglobin HbA (•) and Hb Prisca (■). Solid lines show the non linear cumulant analysis fit.

Novel purified hemoglobin mutants are provided comprising purified mutant β-globin polypeptides having the amino acid sequence of normal human hemoglobin β-globin modified by (i) the substitution or deletion of Cys at positions 93 and 112, and (ii) the substitution of a Cys for a non-Cys amino acid at one other position. This mutation results in the polymerization of hemoglobin tetramers containing the mutant β-globin. The polymerization proceeds through the establishment of disulfide bonds. The tetrameric hemoglobin molecules may be crosslinked to one another through cysteine residues, resulting in the formation of stable polymers that are highly purified. Preferably, Cys is substituted for Ser at position 9, Asn at position 80 or Lys at position 17. The Ser9→Cys substitution is preferred.

Unlike the naturally occurring HbPorto Allegre mutant which contains the same β(Ser9→Cys) substitution, the mutant β-globin of the present invention is further characterized by the deletion or substitution of cysteine residues at β-globin positions 93 and 112. This further modification prevents the formation of spurious S—S bonds during refolding and polymerization. According to a preferred embodiment, Cys93 is replaced by alanine and Cys112 is replaced by glycine, although other substitutions are possible. The resulting three-position mutation in the human hemoglobin β-globin, β(S9C+C93A+C112G) identifies "Hb Prisca".

Since the tetrameric hemoglobin molecule Hb Prisca contains two β-globin molecules and two α-globin molecules, the three-position mutation results in a total of six mutations per tetramer. These mutations allow for proper folding of the recombinant product and increased yield. The mutant tetramers equilibrate to form a homogeneous hemoglobin polymer of seven individual hemoglobin tetramers. The heptamer has a molecular size near 450 kDa. (A single tetramer hemoglobin molecule has a size of 64 kDa)

Normal human α-globin contains a Cys at position 104 SEQ ID NO:5). According to the present invention, the α-globin globins in the tetrameric hemoglobin molecule may contain a mutation whereby the Cys at position 104 is deleted or substituted with a non-cysteine amino acid. Optionally, a further modification may comprise insertion of a Cys into the α-globin chain, or substitution of a Cys residue for another amino acid, at a position other than position 104. For example, Cys may be substituted for Ala at position 71, or Cys may be substituted for Ala at position 53. Preferably, the Cys at α104 is substituted with a non-Cys amino acid, most preferably Ser, and no other Cys residues are contained in the α-globin polypeptide. Set forth as SEQ ID NO:7 and SEQ ID NO:6 are, respectively, the nucleotide and amino acid sequences of the Cys104→Ser α-globin mutant.

According to another embodiment of the invention, the modified hemoglobin has all of the native Cys residues substituted by non-Cys residues. To obtain polymerization, one non-native Cys is introduced into either the α-globin or β-globin polypeptide, by substitution. The substitution for Cys occurs at β-globin Ser9; β-globin Lys17; β-globin Asn80; α-globin Ala 71; or α-globin Ala53. The resulting modified hemoglobin molecule contains two non-native Cys residues per molecule, since each hemoglobin molecule contains two α and two β chains. Polymerization proceeds through the artificially introduced Cys residues.

The polymerization of hemoglobin tetramers containing the Hb Prisca mutation according to the present invention has been observed by light scattering measurements which estimate the radius of the molecules in solution. Dynamic light scattering indicates that the polymer is formed by seven hemoglobin tetramer molecules, and that the polymer is highly homogeneous. The functional characteristics are those of natural human hemoglobin.

Hb Prisca polymerizes to generate a homogeneous globular polymer of human hemoglobin with functional characteristics similar to those of the natural protein. Polymerization of hemoglobin tetramers containing the Hb Prisca mutation to about 5 molecules occurs in 6 days; polymerization to 7 molecules is reached after about 3 months. The oxygen affinity $P_{50}$ (partial pressure of oxygen corresponding to 50% saturation with oxygen) of the heptamer is the same as that of normal tetrameric human hemoglobin (HbA). Moreover, the cooperativity (n), another parameter relevant to oxygen delivering capacity, is maintained on polymerization. The cooperativity (n) is only slightly decreased with respect to native hemoglobin. The heptamer is resistant to autoxidation. The heptamer is highly stable with absence of precipitation and methemoglobin formation during various manipulations and upon storage for 120 days at 4° C.

Since oncotic pressure is proportional to the number of molecules in solution, solutions of the polymerized hemoglobin of the present invention are expected to have a low oncotic pressure per gram of protein, while maintaining a high oxygen carrying capacity.

A model was constructed of R-state Hb Prisca tetramers joined by disulfide bridges between their βCys9 residues. The tetramers were arranged in the best approximation to the corners of a cube without van der Waals interpenetration. The model predicts a location for an eighth tetramer to complete the cube, if the entropic costs of disulfide coupling the eighth tetramer were not so high. This model shows that if the tetramers arranged themselves in the approximation of a cube, the remaining sulfhydryls would not be accessible to additional polymerization after the addition of the seventh molecule.

The amino acid sequences of the normal human α-globin and β-globin polypeptides are known and set forth herein: SEQ ID NO:5 (α-globin); SEQ ID NO:3 (β-globin). The nucleotide sequences encoding the normal polypeptides are also known and set forth herein: SEQ ID NO:12 (α-globin); SEQ ID NO:1 (β-globin).

The mutant hemoglobin β-globins of the present invention may be prepared utilizing well-known expression systems for producing recombinant β-globin in suitable microbial hosts such as *E. coli*. See Fronticelli et al., *J. Prot. Chem.* 10:495–501(1991), Sanna et al., *J. Biol. Chem.* 272: 3478–3486 (1996) and U.S. Pat. No. 5,239,061 to Fronticelli et al., the entire disclosures of which are incorporated herein by reference. Site-specific mutagenesis is used to introduce appropriate mutations into the native β-globin nucleotide coding sequence to provide a mutant DNA encoding the desired mutant β-globin polypeptide.

Similarly, site-specific mutagenesis is used to introduce appropriate mutations into the native α-globin nucleotide coding sequence to provide a mutant DNA encoding the desired mutant α-globin polypeptide. Such α-globin mutants may be prepared, for example, according to the procedures set forth in U.S. Pat. No. 5,661,124 to Hoffman et al., the entire disclosure of which is incorporated herein by reference. Mutants of α-globin may also be prepared using the α-globin expression plasmid, pNFα. The construction of pNFα is described by Sanna et al., *J. Biol. Chem.* 272:3478–3486 (1997), the entire disclosure of which is incorporated herein by reference.

Thus, according to an embodiment of the invention, novel purified and isolated polynucleotides are provided encoding the modified α-globin and β-globin polypeptides of the present invention. The invention is also directed to a method for producing the polypeptides by culturing a suitable microorganism or cell which has been transformed with plasmids which encode the novel polypeptides.

Suitable vectors for use in expressing the modified human hemoglobin of the invention may contain the full DNA sequences coding for α- or β-globin, or the entire DNA sequence coding for hemoglobin including both α- and β-globin. Any suitable vector capable of expressing a protein may be used.

Recombinant mutant β-globin is recovered from cultures by lysing the cells to release the β-globin present inside the cells in the form of fusion protein or as a β-globin molecule per se. Cell debris can be separated by centrifugation. The remaining debris and the supernatant are then repeatedly treated with solvents in which the cell debris are soluble but in which the β-globin is not soluble to thereby precipitate the β-globin. These procedures can be repeated and combined with other procedures including filtration, dialysis and/or chromatography to obtain a pure product. Enzymatic cleavage of the fusion protein may be necessary.

In accordance with degeneracy of genetic code, it is possible to substitute at least one base of the base sequence of a gene by another kind of base without causing the amino acid sequence of the polypeptide produced from the gene to be changed. Hence, the nucleic acids of the present invention encoding mutant or wild-type α- or β-globins may have any base sequence that has been changed by substitution in accordance with degeneracy of genetic code.

The DNA for the globins is readily modified by substitution, deletion or insertion of nucleotides, thereby resulting in novel DNA sequences encoding the mutant α- and β-globins of the present invention. These modified sequences are used to produce mutant α- and β-globins, and mutant hemoglobins containing such mutant globins.

DNA regions are operably linked when they are functionally related to each other. For example, DNA for a presequence or secretory leader is operably linked to DNA for a polypeptide if it is expressed as a pre-protein which participates in the secretion of the polypeptide; a promoter is operably linked to a coding sequence if it controls the transcription of the sequence; or a ribosome binding site is operably linked to a coding sequence if it is positioned so as to permit translation. Generally, "operably linked" means contiguous and, in the case of secretory leaders, contiguous and in reading phase.

Suitable host cells for expressing the mutant globins are prokaryotes, yeast or higher eukaryotic cells. Prokaryotes include gram negative or gram positive bacteria, for example E. coli or Bacilli. Higher eukaryotic cells include established cell lines of insect, spider or mammalian origin.

Generally, a microbial vector will contain an origin of replication recognized by the intended host, a promoter which will function in the host and a phenotypic selection gene, for example, a gene encoding proteins conferring antibiotic resistance or supplying an auxotrophic requirement.

Vectors must contain a promoter which is recognized by the host organism. This is generally a promoter homologous to the intended host. Promoters most commonly used in recombinant DNA construction include the β-lactamase (penicillinase) and lactose promoter systems, a tryptophan (trp) promoter system and the tac promoter. While these are the most commonly used, other known microbial promoters are suitable. Details concerning their nucleotide sequences have been published, enabling a skilled worker operably to ligate them to DNA encoding α- and/or β-globins.

In addition to prokaryotes, eukaryotic microbes such as yeast cultures may be transformed with α- and/or β-globin encoding vectors. *Saccharomyces cerevisiae*, or common baker's yeast, is the most commonly used among lower eukaryotic host microorganisms, although a number of other strains are commonly available. Yeast vectors generally will contain an origin of replication from the 2 micron yeast plasmid or an autonomously replicating sequence (ARS), a promoter, a DNA sequence coding for α- and/or β-globins, sequences for polyadenylation and transcription termination and a selection gene.

Suitable promoting sequences in yeast vectors include the promoters for metallothionein, 3-phosphoglycerate kinase or other glycolytic enzymes. One such yeast vector is described by Wagenbach et al., *Bio Technology* 9:57 (1991).

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the globin coding sequence to provide polyadenylation of the mRNA and termination.

In addition to microorganisms, cultures of cells derived from multicellular organisms may also be used as hosts. In principal, any higher eukaryotic cell culture is workable, whether from vertebrate or invertebrate culture. However, interest has been greatest in vertebrate cells, and propagation of vertebrate cells in culture (tissue culture) has become a routine procedure in recent years. Examples of useful host cell liens are VERO and HeLa cells, Chinese Hamster ovary (CHO) cell lines, and WI38, BHK, COS-7 and MDCK cell lines. Expression vectores for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The modified human hemoglobin of the present invention may also be produced in transgenic animals. Hemoglobins have been produced in transgenic pigs, for example. See U.S. Pat. No. 5,922,854 to Kumar et al.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication. Smaller or larger SV40 fragments may also be used, provided the approximately 250 bp sequence extending from the Hind III site toward the BgII site located in the viral origin of replication is included.

An origin of replication may be provided either by construction of the vector to include an exogenous origin, such as may be derived from SV40 or other viral (e.g., Polyoma, Adenovirus, VSV, or BPV) source, or may be provided by the host cell chromosomal replication mechanism. If the vector is integrated into the host cell chromosome, the latter is often sufficient.

According to one embodiment of the invention, the β-globin and α-globin polypeptides, including mutants thereof, are advantageously expressed as fusion proteins. The normal β-globin polypeptide may be expressed as the fusion protein NS1-FX-β-globin. This fusion protein comprises 81 residues of the flu virus protein NS1, the Factor $X_a$ recognition sequence Ile-Glu-Gly-Arg (SEQ ID NO:8), and the sequence of β-globin. The fusion protein is expressed in *E. coli* AR58 by transformation with plasmid pJKO5, the construction of which is described by Fronticelli et al., *J. Prot. Chem.* 10:495–501(1991), the entire disclosure of which is incorporated herein by reference. The mutant β-globin polypeptides are prepared in the same fashion, substituting the wild type β-globin nucleotide sequence in pJKO5 with the appropriate mutant sequence generated by site-specific mutagenesis. A procedure for introducing mutations in the β-globin nucleotide sequence is described in U.S. Pat. No. 5,239,061. Site-directed mutagenesis may be carried out using standard molecular biological techniques, using standard reagents such as the "Muta-Gene M-13 in vitro Mutagenesis Kit" available from Bio-Rad Laboratories.

According to one embodiment of the invention, the β-globin of Hb Prisca is prepared as follows. The 934 bp fragment from HindIII digestion of pJKO5 is isolated and cloned into the HindIII site of the M13mp18 phage vector, and mutagenesis is carried out with the Bio-Rad kit. The following oligonucleotides are used to introduce the indicated mutations into β-globin, wherein the mutating nucleotides are underlined:

β(Ser9→Cys): 5'-GGC AGT AAC GGC GCA CTT CTC CTC AGG-3' (SEQ ID NO:9);

β(Cys93→Ala): 5'-TGC AGC TTG TCA GCA TGC AGC TCA CTC-3' (SEQ ID NO:10); and

β(Cys112→Gly): 5'-CAG CAC ACC GAC CAG CAC-3' (SEQ ID NO:11).

For expression, the mutated genes are removed from the M13mp18 plasmid with HindIII and ligated back into the 6200 bp fragment obtained from digestion of pJKO5 with HindIII.

Mutants of α-globin are prepared using the α-globin expression plasmid, pNFα, which is structurally analogous to pJKO5. The construction of pNFα is described by Sanna et al., *J. Biol. Chem.* 272:3478–3486 (1997), the entire disclosure of which is incorporated herein by reference. Expression of the plasmid in *E. Coli* strain AR120 yields large amounts of the NS1-FX-α-globin fusion protein, which is analogous to the NS1-FX-β-globin fusion protein. Mutagenesis is carried out with the appropriate mutagenizing oligonucleotides, as with pJKO5, to yield the desired α-globin mutants.

The partially purified fusion proteins may be dissolved in alkali and partially renatured by extensive dialysis at pH 8 to 9 in the presence of an S—S bond reducing agent. After enzymatic cleavage with factor Xa, the globin polypeptide separates. The isolated β and α polypeptides may be combined and heme added to reconstitute tetrameric hemoglobin. It may be appreciated that the reconstituted hemoglobin may comprise mutant β-globin and native α-globin, or both mutant β-globin and mutant α-globin. To form a functional hemoglobin molecule, it is necessary to join the α- and β-globins, and provide the prosthetic heme groups. Procedures for the purification of cloned mutant β-globin and reconstitution of tetrameric hemoglobin are disclosed in U.S. Pat. No. 5,239,061.

Upon treatment of the tetrameric hemoglobin with p-chloromercuribenzoate (Bucci and Fronticelli, *J. Biol. Chem.* 240, PC551, 1965), the α and β mutant chains can be separated in their native state. Mixing of the separated native state mutant α and β chains gives a tetrameric hemoglobin carrying mutations in both α- and β-globins.

In one embodiment, both the β-globin and α-globin polypeptides are recombinantly produced. In such cases, it is desirable to co-express the polypeptides in the same expression system. One such co-expression system is described in U.S. Pat. No. 5,753,465 to Ho et al., the entire disclosure of which is incorporated herein by reference. The expression method utilizes a plasmid, pHE2, in which the synthetic human α- and β-globin genes and the Met-AP gene for *E. coli* are arranged in tandem in the same orientation and are co-expressed under the control of separate tac promoters. The coding sequence the *E. coli* Met-AP gene is contained in ATCC 53245 and U.S. Pat. Nos. 4,865,974, 4,870,017 and 5,013,662, the entire disclosures of which are incorporated herein by reference. The coding sequence is inserted into the EcoRI and HindIII sites of the HbA expression plasmid pDLIII-13e, the construction of which is disclosed by Hoffman et al., *Proc. Natl. Acad. Sci. USA* 87:8521 (1993), the entire disclosure of which is incorporated herein by reference. The resulting plasmid, pTC-EM2, contains the complete coding sequence of the *E. coli* Met-AP gene flanked by the tac promoter and 5ST1T2 terminators from pDLIII-13e.

The resulting co-expression plasmid contains two expression cassettes arranged in tandem in the same orientation as follows: (1) tac promoter-*E. coli* Met-AP coding sequence-5ST1T2 terminator and (2) tac promoter-α-globin coding sequence-β-globin coding sequence-5ST1T2 terminator. See FIG. 1 of the Ho et al. patent.

The modified hemoglobin polymers of the present invention may be incorporated into physiologically acceptable blood substitute solutions. One such solution may be based upon the solution described in U.S. Pat. No. 5,028,588 to Hoffmann et al. The solution contains from about 6 to about 120 g/L hemoglobin polymer, from about 135 to about 145 mEq/L sodium, from about 3.5 to about 4.5 mEq/L potassium, and from about 90 to about 100 mEq/L chloride. Preferably, the solution has a pH of 7.3–7.5, an osmolarity of 280–310, and an oncotic pressure of 20–30 mm Hg. Glucose may be optionally added to adjust the osmolarity. Additional agents such as albumin, dextran and polyethylene glycol, in the amount suggested in U.S. Pat. No. 5,028,588, may be added to increase oncotic pressure. Antioxidants and/or free radical scavengers such as mannitol, glutathione, ascorbic acid or vitamin E may also be included.

The blood substitute may be administered to a patient in any situation requiring supplementation of the oxygen-carrying capacity of the patient's blood. The amount of the blood substitute administered will depend on the size, weight and age of the patient, the clinical condition of the patient, and the degree of impairment of the natural oxygen-carrying capacity of the patient's blood. Herein, an "effective amount" of blood substitute is any amount which brings about a clinically relevant enhancement of the oxygen-carrying capacity of the patient's blood over a clinically meaningful time interval.

The practice of the invention is illustrated by the following non-limiting examples.

EXAMPLE 1

Preparation of Mutant and Wild Type β-Globin Fusion Protein Vector

The construction of the plasmid pJKO5 is described by Fronticelli et al., *J. Prot. Chem.* 10:495–501(1991), the entire disclosure of which is incorporated herein by reference. The vector is a derivative of pASI (Rosenberg, et al. (1982) *Met. Enzymol.* 101, 123), where the NS1 gene from influenza A virus is cloned into the Bam HI site (Young, et al. (1983) *Proc. Natl. Acad. Sci USA* 80, 6105). A linker coding for the recognition sequence of blood clotting Factor $X_a$ is inserted into the NcoI site of the NS1 gene. The human β-globin cDNA (obtained by Dr. B. Forget, Yale University) is inserted 3' to the factor $X_a$ recognition sequence giving a plasmid similar to the described previously by Nagai and Thogersen (1984), *Nature* 308, 810. High expression levels of the NS1-FX-β-globin fusion protein are obtained using *E. coli* AR58 transformed with this plasmid. The fusion protein comprises 81 residues of protein NS1, and the Factor Xa recognition sequence Ile-Glu-Gly-Arg (SEQ ID NO:8), and β-globin. The fusion protein is expressed in *E. coli* AR58 by transformation with plasmid pJKO5.

For mutagenesis, plasmid pJKO5 was subjected to HindIII digestion. The 934 bp digestion fragment was isolated and cloned into the HindIII site of the M13mp18 phage vector. Mutagenesis was carried out on the resulting plasmid using the Muta-Gene mutagenesis kit (BioRad) and the following oligonucleotides where mutating nucleotides are underlined:

β(Ser9→Cys): 5'-GGC AGT AAC GGC G<u>CA</u> CTT CTC CTC AGG-3' (SEQ ID NO:9);

β(Cys93→Ala): 5'-TGC AGC TTG TC<u>A GCA</u> TGC AGC TCA CTC-3' (SEQ ID NO:10); and β(Cys112→Gly): 5'-CAG CAC AC<u>C</u> GAC CAG CAC-3' (SEQ ID NO:11).

The mutated gene was removed from the M13mp18 plasmid with HindIII and ligated back into the 6200 bp fragment obtained from digestion of pJKO5 with HindIII.

EXAMPLE 2

Preparation of Mutant and Wild Type α-Globin Fusion Protein Vector

Vectors for expression of mutant α-globin may be prepared by mutagenizing the α-globin expression plasmid pNFα. The construction of the latter is described by Sanna et al., *J. Biol. Chem.* 272:3478–3486 (1997), the entire disclosure of which is incorporated herein by reference. The α-globin expression plasmid, pNFα, is structurally identical to pJKO5 except that the α-globin cDNA replaces the β-globin cDNA of pJKO5. For mutagenesis, plasmid pNFα is subjected to HindIII digestion and the 934 bp digestion fragment is isolated and cloned into the HindIII site of the M13mp18 phage vector, followed by mutagenesis with the appropriate oligonucleotides to introduce the desired change, e.g., the substitution of Cys104 to a non-cysteine amino acid, in the amino acid sequence of α-globin.

EXAMPLE 3

Expression, Reconstitution and Purification of Recombinant Hemoglobin Containing Mutant β-Globin (Hb Prisca)

Growth, expression and purification of recombinant β-globin, and reconstitution and assembly of recombinant β-globin with α-globin into tetrameric hemoglobin, followed protocols previously described by Fronticelli et al., *J. Prot. Chem.* 10:495–501(1991), Sanna et al., *J. Biol. Chem.* 272: 3478–3486 (1996), with modifications. *E. coli* strain AR120 was transformed with the mutant pJKO5 vector prepared above. Cells were grown in a fermentor at 37° C. in an LB plus ampicillin media to an $OD_{600}$ of 0.600. Nalidixic acid was added (60 μg/ml) and the growth continued for 4 hours. The cells were harvested either by centrifugation or using a Pellicon Cassette. The fusion protein was separated from most of the other cell components by washes with deoxycholate and Triton X-100. The insoluble pellet collected by centrifugation contained the fusion β-globin protein along with some other residual proteins. The pellets were solubilized quickly in a minimum volume of 50 mM cold NaOH and diluted 10-fold with 40 mM borate buffer at pH 8.4. This sample was digested with Factor $X_a$ in the ratio 1:200 in the presence of 1 mM $Ca^{2+}$ for 24 hours. The extent of enzymatic cleavage was monitored by reverse phase HPLC using a Vydac C4 column. Upon cleavage with Factor $X_a$, the protein was diluted to 2 mg/ml ($OD_{280}$=1.0 is taken as 1 mg/ml) with 0.04 M borate buffer at pH 9.0+0.002 M EDTA. In order to dissolve the aggregates, the solution was deoxygenated by stirring under a constant stream of $N_2$ followed by addition of dithiothreitol (DTT) to a final concentration of 0.001 M. After 24 hours at 4° C. the protein was reconstituted with CN-heme and native partner α-subunit prepared from carboxy HbA by reaction with p-chloromercuribenzoate (Bucci and Fronticelli, *J. Biol. Chem.* 240, PC551, 1965). After one week the protein was concentrated and the heme converted to the carbonmonoxy derivative by passage of the sample on a Sephadex 25G column, equilibrated with 0.1 M Phosphate buffer pH 7.3+0.03 mM DTT saturated with carbon monoxide (CO), to which 2 ml Na-dithionite (100 mg/ml) had been previously absorbed. The hemoglobin was purified on an affinity column of immobilized hemoglobin (Rossi Fanelli et al., *Eur. J. Biochem.* 92:253–259:1978; Chiancone et al., *J. Chromatogr.* 604:117–123, 1992). All the purification steps were performed in the presence of 0.03 mM DTT in order to avoid any S—S formation during the purification procedure. After purification of the tetrameric mutant Hb, the DTT present in the solution was removed by passage through a G25 Sephadex column, equilibrated with a buffer containing 50 mM Hepes+100 mM NaCl+1 mM EDTA saturated with CO. This step is referred to as the "zero polymerization time". The sample was concentrated in the cold to 1.5–2.0 mM for 120 days.

EXAMPLE 4

Measurement of Dispersivity of Hb Prisca Polymer by Dynamic Light Scattering

The radius of Hb Prisca was measured as follows by dynamic light scattering. The radius was measured at time zero prior to the removal of DTT, while measurements at increasing time were recorded after removal of the DTT.

A. Methods

Dynamic light scattering measurements were performed using the instrument DynaPro-801. A Diode laser provides a light source at 783 nm. The diffused light was collected at a scattering angle of 90° through fiber optics and converted to an electrical signal by an avalanche photo diode. The scattering cell is a flow-through type and the inlet and outlet ports are designed such that the flow pattern would sweep the entire cell volume, allowing maintenance of a low number as possible the number of foreign particles in the scattering volume by carefully cleaning of the cell prior to the measurements. The hemoglobin in the carbonmonoxy form was at a concentration between 1 and 2 mg/ml in 50 mM Hepes+100 mM NaCl+1 mM EDTA buffer at pH 7.4 equilibrated with CO. The samples were slowly injected into the scattering cell through a series of Whatman inorganic membrane filters with decreasing porosity from 0.1 μm to 0.02 μm.

The time-dependent autocorrelation function (ACF) of the photon current was then computed with a software correlator (based on a DSP unit) with 83 channels. Every 10 seconds an ACF was collected with $10^5$–$10^6$ counts depending on sample concentration. That ACF was summed to the running ACF, only when the fitted single exponential baseline agreed with the average counts number within 0.3%. This process was stopped when the running ACF reached $10^7$ counts. At least 5 intensity ACF were collected and then fitted to a second order cumulant function of equation 1 (Koppel., *J. Chem. Phys.*, 57:4814–4820;1972), $$G(t_i) \leftarrow bl \left\{ 1 + sn \left| \exp\left( -\Gamma_1 t_i + \frac{1}{2}\Gamma_2 t_i^2 \right) \right|^2 \right\} \quad (1)$$

where $G(t_i)$ is the ACF, t is the time, bl is the baseline, sn is a parameter related to the signal to noise ratio, and $\Gamma_1$ and $\Gamma_2$ are the first and the second cumulant, respectively.

The average radius R is obtained from the first cumulant $\Gamma_1$ by equation 2, $$R = \frac{k_B T q^2}{6\pi\eta\Gamma_1} \text{ where } q^2 = \frac{4\pi n}{\lambda_0} sen\left(\frac{\theta}{2}\right) \quad (2)$$

where $k_B$ is the Boltzmann constant, n is the index of refraction of the solution (which depends slightly on buffer and protein concentration), q is the scattering vector, θ is the scattering angle, and η is the solvent viscosity at the experimental temperature T (° K). The latter has been checked within the accuracy of 0.1° C. with a thermocouple positioned close to the scattering cell, and it remained within ±2 deg. C. of 24° C. for the duration of the experiment. $\lambda_0$ is the wavelength of incident light.

The ratio of the first two cumulants gives the sample polydispersivity (Q) according to equation 3:

$$Q = \frac{\Gamma_2}{\Gamma_1^2} \quad (3)$$

B. Results

Table I reports the radius of HbA as compared to the radius of Hb Prisca at time zero and at increasing polymerization time. The same values were derived from a non linear single exponential fitting procedure of the actual data and from the cumulant analysis of ACF (Eq 2). The number of tetrameric hemoglobins polymerized, p, was calculated from the cubic power the ratio of the radius of the polymer over that of tetrameric HbA, assuming that these proteins have a spherical shape at the protein concentration of 1–2 mg/ml. Alternatively this calculation was repeated, considering that at the concentration of the measurements the HbA solution contained 10% dimers, i.e. the tetramer radius is derived by equation 4, with α=0.1:

$$R_T = R_{HbA} \frac{2(1-\alpha) + \alpha^3 \sqrt{2}}{2-\alpha} \quad (4)$$

$P_{50}$ in Table I represents the oxygen affinity at 50% oxygen saturation and n the cooperativity of the system.

five tetrameric molecules. The highest degree of polymerization was attained after 45 to 90 days consistent with the decreased motion of the polymeric molecules.

Figure 2:
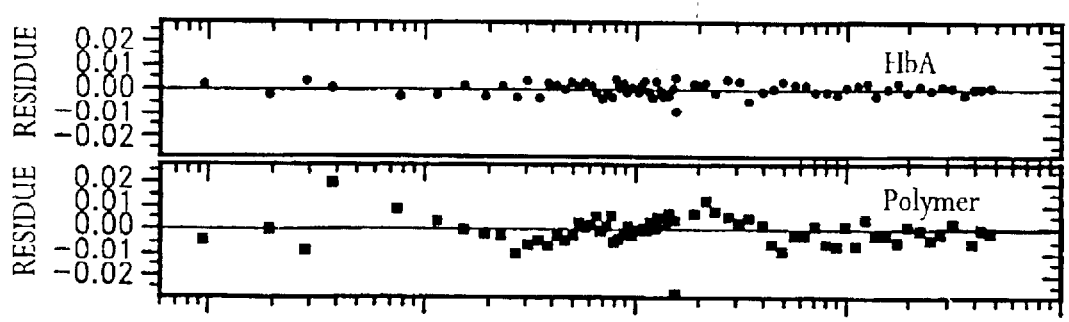
FIG. 2 shows the residual of the analysis for HbA and Hb Prisca ("Polymer").

The non-linear fit cumulant analysis (Eq. 1) of HbA and of Hb Prisca at 110 days polymerization time is shown in FIGS. 1 and 2. The shift of Hb Prisca toward the right indicates a slower decay rate, consistent with a larger radius of the polymer. The residual for the analysis of the polymerized Hb Prisca in comparison to unpolymerized HbA indicates the presence of a homogeneous population in the polymerized mutant hemoglobin.

Figure 3:
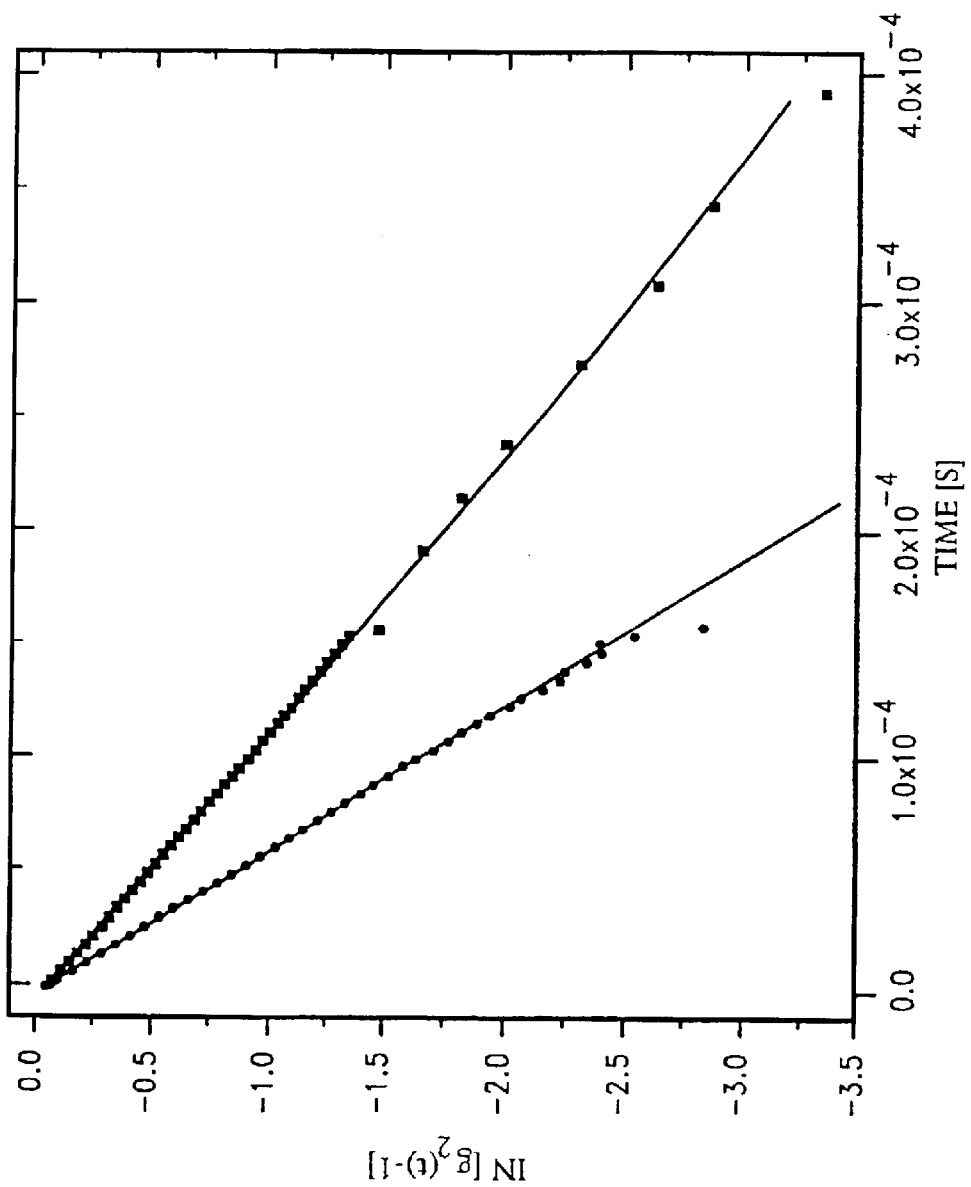
FIG. 3 shows the ACF for HbA (•) and Hb Prisca (■) transformed according to the cumulant analysis method. Solid lines are a second order polynomial fit of the transformed data.

The linear cumulant analysis of HbA and of Hb Prisca at 110 days polymerization time is compared in FIG. 3. For each protein the results from five different measurements are reported; they are very similar. The different slope of HbA and Hb Prisca again reflects the different size of the two samples. The two samples have a remarkable similar linearity, consistent with the presence of a highly homogeneous population.

The values of polydispersivity Q, (Table I) representing the deviation from a perfect homogeneous sample (Q=0), is 0.02±0.02 for HbA, indicating the perfect monodispersivity of this sample and 0.07±0.02 for Hb Prisca at 110 days polymerization time. The small polydispersivity calculated for Hb Prisca indicates that the amount of non homogeneous population present in the polymerized sample, is very small.

EXAMPLE 5

Functional Characterization of Hb Prisca

A. Methods

Aliquots were taken at time intervals during polymerization for oxygen binding measurements. Prior to measurements, CO was removed photolysis under a stream of oxygen. Measurements were performed using the thin layer dilution technique of Dolman and Gill (*Anal. Biochem.* 87:127–134, 1978) with an AVIV 14DS spectrophotometer. In this technique the oxyhemoglobin is deoxygenated by stepwise dilution of the equilibrating gas with constant volumes of $N_2$. Formation of methemoglobin as judged by spectral deconvolution of the initial and final spectra was

TABLE I

Biophysical Parameters of HbA and Hb Prisca

| Protein | Time (days) | R (nm) | p | p* | Q | $P_{50}$ (mmHg) | n |
|---|---|---|---|---|---|---|---|
| HbA | — | 3.19 ± 0.01 | — | — | 0.02 ± 0.02 | 4.0 | 2.9 |
| Hb Prisca | 0# | 3.33 ± 0.05 | 1.14 ± .05 | 1.09 ± .05 | | 3.9 | 2.4 |
| Hb Prisca | 6 | 5.61 ± 0.01 | 5.44 ± .06 | 5.22 ± .06 | | 4.7 | 2.5 |
| Hb Prisca | 45 | 6.00 ± 0.05 | 6.65 ± .18 | 6.39 ± .17 | | 4.2 | 2.4 |
| Hb Prisca | 90 | 6.21 ± 0.02 | 7.38 ± .10 | 7.08 ± .09 | | 4.0 | 2.5 |
| Hb Prisca | 110 | 6.20 ± 0.01 | 7.34 ± .08 | 7.05 ± .07 | 0.07 ± 0.02 | 4.4 | 2.4 |

*Number of tetrameric molecules polymerized, assuming the presence of 10% αβ dimers in HbA
These measurements were carried out in the presence of 1 mM DTT At zero time the hydrodynamic radius of HbA and Hb Prisca was the same. After removal of DTT, the hydrodynamic radius rapidly increased to indicate the polymerization of less than 5%. Protein concentration was 1.5–2.0 mM in heme, in 50 mM HEPES+100 mM NaCl+1 mMEDTA buffer at pH 7.4 at 24° C. The experimental data were fitted to the Adair equation using an iterative procedure incorporating the Marquardt algorithm, $$Y = \frac{\beta_1 p(O_2) + 2\beta_2 p(O_2)^2 + 3\beta_3 p(O_2)^3 + 4\beta_4 p(O)^4}{4[1 + \beta_1 p(O_2) + \beta_2 p(O_2)^2 + \beta_3 p(O_2)^3 + \beta_4 p(O_2)^4]} \quad (5)$$

where Y is the fractional saturation with $O_2$, $P(O)_2$ is the partial pressure of oxygen in millimeters of mercury and $\beta_{i's}$ are the overall Adair constants related to the intrinsic statistical affinity constant Ki of the subsequent steps of oxygenation by $\beta i=\Pi_r Ki$. The value of the median ligand activity Pm, was determinated using the relation $Pm=\beta 4^{-0.25}$ (Wyman, J and Gill, S. J. *Binding and Linkage: Functional Chemistry of Biological Molecules*. University Science Books. Mill Valley, Calif.)

B. Results

The functional parameters of Hb Prisca calculated at increasing polymerization time are listed in Table I, above. The functionality at pH 7.4 was not modified by the extent of polymerization. This indicates that the intermolecular crosslinking at the two external β9Cys and the packing of the seven hemoglobin molecules do not introduce conformational constraints to either the tertiary or quaternary structure which affect the functionality at physiological pH.

FIG. 4 contains the oxygen binding curves of natural HbA and of Hb Prisca at 110 days polymerization time are shown. The two hemoglobins have a similar oxygen affinity, but the cooperativity of Hb Prisca, although good (n=2.4), is decreased with respect to HbA (n=2.9). See FIG. 5. A similar decrease in cooperativity is observed in the wild type of the recombinant hemoglobins prepared with the same expression system (Fronticelli et al., *J. Biol. Chem.* 270:30588–30592 (1995), Sanna et al., *J. Biol. Chem.* 272: 3478–3486 (1996)), and in the β cysteine single and double mutants, in similar experimental conditions of buffer and Cl⁻ concentration (Dolman and Gill, supra). Thus, the observed decrease in cooperativity observed in Hb Prisca is intrinsic to the system and should not be attributed either to the mutations or to the polymerization phenomenon. This is at variance with glutaraldehyde polymerization of HbA which gives a highly heterogeneous product with a largely reduced cooperativity (n=1.3–1.5) (Doyle et al., *J. Biol. Chem.* 274:2583–2591, 1999; MacDonald & Pepper, *Methods in Enzymology* 231:287, 1994).

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A human β-globin mutant polypeptide comprising the amino acid sequence of the normal human β-globin (SEQ ID NO:3) modified by (i) the substitution or deletion of Cys at positions 93 and 112, and (ii) the substitution of a Cys for a non-Cys amino acid at one other position in the polypeptide.

2. A mutant polypeptide according to claim 1 wherein Cys is substituted for one of the amino acids at the following positions:
   (a) Ser at position 9;
   (b) Asn at position 80; or
   (c) Lys at position 17.

3. A mutant polypeptide according to claim 1 wherein Cys is substituted for Ser at position 9.

4. A mutant polypeptide according to claim 3 having the amino acid sequence SEQ ID NO:4.

5. A modified human hemoglobin comprising a β-globin polypeptide according to claim 1.

6. A modified human hemoglobin comprising a β-globin polypeptide according to claim 4.

7. A modified human hemoglobin according to claim 5 or 6 comprising a mutant human α-globin polypeptide comprising the amino acid sequence of normal human α-globin (SEQ ID NO:5) modified by the substitution or deletion of Cys at position 104.

8. A modified human hemoglobin according to claim 7 wherein the mutant human α-globin polypeptide is further modified by either the substitution of Cys for Ala at position 71, or the substitution of Cys for Ala at position 53.

9. A modified human hemoglobin comprising:
   a mutant human α-globin polypeptide comprising the amino acid sequence of normal human α-globin (SEQ ID NO:5) modified by the substitution of Cys at position 104 by a non-Cys amino acid;
   a mutant human β-globin polypeptide comprising the amino acid sequence of normal human β-globin (SEQ ID NO:3) modified by the substitution of Cys at positions 93 and 112 by non-Cys amino acids; and
   said modified hemoglobin further characterized by the substitution of Cys for the native sequence amino acid at one of the following positions:
   β-globin position 9;
   β-globin position 17;
   β-globin position 80;
   α-globin position 71; or
   α-globin position 53.

10. A polymeric hemoglobin comprising a modified human hemoglobin according to claim 5, 6 or 9, wherein adjacent hemoglobins are covalently bonded to each other by one or more disulfide bridges formed by cysteine amino acid residues.

11. A polymeric hemoglobin according to claim 10 wherein the modified hemoglobin is characterized by the substitution of Cys for the native sequence amino acid at β-globin position 9, said polymeric hemoglobin comprising seven modified hemoglobins.

12. A blood substitute comprising a polymeric hemoglobin according to claim 10.

13. A blood substitute comprising a polymeric hemoglobin according to claim 11.

14. A mutant human α-globin polypeptide comprising the amino acid sequence of normal human α-globin (SEQ ID NO: 5) modified by the substitution or deletion of Cys at position 104 and either the substitution of Cys for Ala at position 71 or the substitution of Cys for Ala at position 53.

15. A nucleotide sequence encoding a mutant polypeptide according to claim 4.

16. A nucleotide sequence according to claim 15 which comprises the nucleotide sequence SEQ ID NO:2.

17. A vector comprising a promoter operably linked to a nucleic acid sequence according to claim 15, capable of directing the expression of a mutant human β-globin polypeptide.

18. A host cell transformed with a vector according to claim 17.

19. A method for producing a human β-globin mutant polypeptide comprising:

growing a culture of transformed host cells of claim 18 under conditions conducive to the expression of said polypeptide by said host cells.

20. A method of supplementing the oxygen-carrying capacity of a patient's blood comprising administering to the patient an effective amount of the blood substitute according to claim 12.

21. A method of supplementing the oxygen-carrying capacity of a patient's blood comprising administering to the patient an effective amount of the blood substitute according to claim 13.

* * * * *